US006872399B2

(12) United States Patent
Polyakov et al.

(10) Patent No.: US 6,872,399 B2
(45) Date of Patent: Mar. 29, 2005

(54) DERMATOMYCOSIS VACCINE

(75) Inventors: Igor Dimitriesich Polyakov, Moscow (RU); Ludmilla Ivanova, Moscow (RU)

(73) Assignee: Boehringer Ingelheim Vetmedica GmbH, Ingelheim (DE)

( * ) Notice: Subject to any disclaimer, the term of this patent is extended or adjusted under 35 U.S.C. 154(b) by 8 days.

(21) Appl. No.: 10/085,703

(22) Filed: Feb. 28, 2002

(65) Prior Publication Data

US 2002/0155134 A1 Oct. 24, 2002

Related U.S. Application Data

(63) Continuation of application No. 09/256,915, filed on Feb. 24, 1999, now abandoned, which is a continuation of application No. 08/568,063, filed on Dec. 6, 1995, now abandoned, which is a continuation of application No. 08/281,380, filed on Jul. 26, 1994, now abandoned, which is a continuation of application No. 08/081,299, filed as application No. PCT/EP92/02391 on Aug. 11, 1993, now abandoned.

(30) Foreign Application Priority Data

Oct. 21, 1991 (RU) .............................. 5006861/13/073089

(51) Int. Cl.$^7$ ...................... A61K 39/00; A61K 39/35; C12N 1/20; C12N 1/16; C12N 1/06
(52) U.S. Cl. ................................ 424/274.1; 424/184.1; 424/275.1; 435/252.1; 435/252.4; 435/254.1; 435/254.6; 435/256.7; 435/259; 435/260
(58) Field of Search .......................... 424/184.1, 275.1, 424/274.1; 435/252.1, 252.4, 254.1, 254.6, 256.7, 259, 260

(56) References Cited

U.S. PATENT DOCUMENTS

| | | | |
|---|---|---|---|
| 4,129,647 A | | 12/1978 | Klein |
| 4,229,434 A | | 10/1980 | Arutjun et al. |
| 4,368,191 A | * | 1/1983 | Sarkisov et al. |
| 4,657,761 A | | 4/1987 | Pinto |
| 5,277,904 A | * | 1/1994 | Pier |
| 5,284,652 A | * | 2/1994 | Pier |
| 5,453,273 A | * | 9/1995 | Werner et al. |
| 6,132,733 A | * | 10/2000 | Werner et al. |
| 6,290,950 B1 | * | 9/2001 | Poliakov et al. |
| 6,428,789 B1 | * | 8/2002 | Strobel et al. |
| 6,723,328 B2 | * | 4/2004 | Strobel et al. ............ 424/274.1 |
| 2002/0155134 A1 | * | 10/2002 | Polyakov et al. ........ 424/274.1 |
| 2002/0187155 A1 | * | 12/2002 | Strobel et al. ............ 424/184.1 |

FOREIGN PATENT DOCUMENTS

| | | |
|---|---|---|
| EP | 0393371 | 10/1990 |
| WO | WO 9307894 | 4/1993 |
| WO | WO9307894 | * 4/1993 |

OTHER PUBLICATIONS

Pavlas et al Veterinárni Medicina 24(LII) Nr. 4 pp 209–215, 1979.*
Wawrzkiewicz et al Med. Weter. 47/7:317–320, 1991.*
Douparinova et al Nauki, 15/1: 74–77 Abstract only, 1978.*
Golovina etal, Byulleten Vsesoyuznogo Instituta Eksperimental'noi Veterinarii 45:59–61, 1982, (Abstract only).*
Pier et al, J. Med & Vet. Mycology, 33:93–97, 1995.*
Wabacha et al, JI 9. Afr. Vet. Ass. 69/4:172–173, 1998.*
Wawrzkiewicz et al, Comp. Immunol. Microbiol,Infect. Dis. 15/1:31–40, 1992.*
Polyakov et al Byulleten Vsesoyuznogo Instituta Eksperimental'noi Veterinarii 65:43–45, 1988 (abstract only).*
Sarkisov, Mikol Fitopatol 19/1: 51–57 (abstract only), 1985.*
Bababanoff Dermatosen in ●Beruf und Umwelt 33/5: 170–174 (abstract), 1985.*
Woloszyn et al Mea. Weter. 37/7: 387–391 1983.*
Aamodt et al, Zbl. Vet. Med. B, 29: 451–56. 1982.*
Kamionowski et al Zycio Weterynaryjne 76/2: 101–102 Abstract only, 2001.*
Woloszyn et al Medycyna Weterynaryjna 52/8: 518–521 (abstract), 1996.*
Qvanova et al, Mikol Fitopatol, 17/5: 363–367 (abstract), 1984.*
Sarkisov et al Veterinariya (Moska) 10: 31–35 (abstract), 1989.*
A.J. Chanis, Dissertation, J.R. Kovalenko Institute, Moskow (Feb. 27, 1989) E.L. Kenney and M. Huppert., "Immunization Against Superficial Fungous Infection", J. Invest. Derm., 32, pp. 7–13 (1959) ("Chanis").
E.L. Kenney and M. Huppert., "Immunization Against Superficial Fungous Infection", J. Invest. Derm., 32, pp. 7–13 (1959).
K. Wawrzkiewicz and J. Wawrzkiewicz, "Early Immunization of Calves with an Inactivated Vaccine Against *Trichophytosis*", Polskie Archiwum Weterynaryjne, 28, pp. 5–16 (1988).
K. Wawrzkiewicz and J. Wawrzkiewicz, "Effect of Levamisole on the Immune Response of Guinea Pigs Immunized with Inactivated Trichophylon verrucosum Strain", Annales UMCS (Lublin), section DD, 39, pp. 53–63 (1984).

(Continued)

*Primary Examiner*—N. M. Minnifield
(74) *Attorney, Agent, or Firm*—Robert P. Raymond; Susan K. Pdcchiari; Mary-Ellen M. Devlin

(57) ABSTRACT

The present invention relates to the preparation of universal inactivated vaccines and their use in preparing compositions for the prophylaxis and therapy of dermatomycosis. Vaccines according to the present invention have the advantage of conferring immunity against all important causes of dermatomycosis in animals and are characterized by stable immunogenic properties, easy preparation, high content of microconidia and lack of side reactions in animals.

2 Claims, No Drawings

OTHER PUBLICATIONS

P. Kielstein and W. Richter, "Versuche zur Immunprophylaxe der Rindertrichophytie", Sonderdruck aus dem Archiv fur Experimentelle Veterinarmedizin Bd. 24, H. May 1970, pp. 1205–1218 (1970) ("Kielstein").

E. Florian et al., "Aktiv Immunizalasi Kiserletek Borjak Tarlosomore Ellen", Magyar Allatorvosok Lapja, 19(12), pp. 529–530 (1964) ("Florian").

M.L. Wharton et al., "Active Immunization Against Trichophyton Purpureum Infection in Rabbits", J. Invest. Dermatol. 14, pp. 291–303 (1950).

C. Mosher et al., "Ringworm (*Microsporum canis*) with inactivated Fungal Vaccine", Vet Med/Small Animal Clin., 72, pp. 1343–1345 (1977).

E. Ibragimov et al., "Investigation of the immunogenic and curative features of a formaldehyde vaccine against ringworm in cattle", Usbek Veterinary Research Institute XXX Part 1 Taskent (USSR) (1980) ("Ibragimny").

K. Wawrzkiewicz et al., "Szczepionka Inaktywowana w Profilaktyce i Leczeniu Grzybicy Skornej Bydla", Medycyna Weterynaryjna, 44(11), pp. 648–651 (1988) ("Wawrzkiewics–Medycyna").

CAB International Abstract No. 892290473 (1989) ("CAB Abstract").

T. Kocik, "Proba Oceny Wartosci Immunogennych Szczepionek Zywych i Zabitych Przeciwko Trychofitozie Dla Swinek Morskich I Miodego Bydla", Polskie Archivum Weterynarynje, 23(3), pp. 95–107 (1982).

Anon, "Results of a Therapeutic Efficacy Test Using an Inactivated Microsporum Canis Vaccine", typewritten material 5–88 available at US Dept. of Agriculture, National Agricultual Library (1988).

R. Weiss et al., "Immunisierungsversuche an Meerschweinchen mit einem Trichophyton Verrucosum–Lebendantigen", Mykosen, 20 (2), pp. 54–64 (1977).

A.K. Sarkisov et al., Biological Abstracts, vol. 81, Abstract No. 4165 (1986).

W. Wawrzkiewicz et al., Biological Abstracts, vol. 92, Abstract No. 124650 (1991).

A.K. Sarkisov et al., "Specific Prophylaxis of *Trichophytosis* in Animals", Mikol. Fitophatol., 19(1), pp. 51–57 (1985).

W. Wawrzkiewicz et al., "An Inactivated Vaccine Against Ringworm", Comp. Immu. Microbiol. Infect. Dis., 15(1), pp. 31–40 (1992).

C.L. Mosher et al., "Treatment of Ringworm (*Microsporum canis*) with Inactivated Fungal Vaccine", Vet. Med., pp. 1343–1345 (Aug. 1977).

R. Gudding et al., "Vaccination of Cattle Against Ringworm Caused by Trichophyton verrucosum", Am. J. Vet. Res., 47(11), pp. 2415–2417 (1986).

Polyakov et al., "Clinical Manifestations of Dermatomycosis induced...", Byulleten Vsesoyuznogo Institute Experimental noi Vet., 65, pp. 43–45 (1988).

Sarkisov et al., "Dermatomycosis of Camels and Biological Properties of the Causal Agent", Veterinariya (Moskva), 10, pp. 31–35 (1989).

Ivanova et al., "Trichophyton sarkisovii New Species, A New Pathogenic...", Mikol. Fitopatol., 17(5), pp. 363–367 (1983).

Segal, "Immunization Against Fungal Diseases in Man and Animal" in Handbook of Applied Mycology, vol. 2, pp. 341–368 (1991).

Grappel et al., "Immunology of Dermatophytes and Dermatophytosis", Bacteriological Riev., 38(2), pp. 222–250 (1974).

A.C. Pier et al; Experimental immunity to Microsporum canis and cross reactions with other dermatophytes of veterinary importance; Journal of Medicine and Veterinary Mycology: (1995) vol. 33 pp. 93–97.

Roar Gudding et al; Immunoprophylaxis of bovine dermatophytosis; Can Vet J; vol. 36 pp. 302–306 (May 1995).

J.K. Wabacha et al; Occurence of dermatophytosis (ringworm) due to Trichophyton verrucosum in dairy calves and its spread to animal attendants; JI S. Afr. vet. Ass. (1998) vol. 69 No. 4 pp. 172–173.

M. Pavlas et al; The Therapeutic and Preventive Effectiveness of Vaccine Against Trichophytosis in Cattle; Research Institute of Veterinary Medicine (1979) vol. 24 No. 4 pp. 209–215.

J. Wawrzkiewicz et al; Monovalent and Combined Inactivated Killed Vaccines in the Prophylaxis of Trichophytosis of Breeding Foxes; Med Weter (1991) vol. 47 No. 7 pp. 317–320.

Douparinova, M. et al; Epidemiological aspects of ringworm in calves on large farms; Central Vet. Res. Inst. (1978) vol. 15 No. 1 pp. 74–77.

Golovina, N.P. et al; Pathogenicity and immunogenicity of strains of Trichophyton verrucosum from different sources; Byulleten Vsesoyuznogo Inst. (1982) vol. 45 pp. 59–61.

Kamionowski, M. et al; Efficacy of Alpevac (Biowet Pulawy) in the prevention of dermatomycosis in rabbits; Zycie Weterynaryjne (2001) vol. 76 No. 2 pp. 101–102 Issn: 0137–6810.

Woloszyn, S. et al; Efficacy of Vaccines in the control of dermatomycoses in rabbits; Medycyna Weterynaryjna (1996) vol. 52 No. 8 pp. 518–521 ISSN: 0025–8628.

Balabanoff V.A.; Occupational dermatomycoses of zoophilic origin in Bulgarial; Dermatosen in Burf und Umwelt (1985) vol. 33 No. 5 pp. 170–174.

Woloszyn, S. et al; Prevalence and specific prevention against trichophytosis in breeding foxes; Med Weter (1983) vol. 39 No. 7 pp. 387–391.

O. Aamondt et al; Vaccination of Norwegian Cattle against Ringworm; Vet. Med B (1982) vol. 29 pp. 451–456 ISSN: 0721–1856.

Eivind Liven et al; Efficacy of vaccination against ringworm in cattle; Nord Vet. Med. (1985) vol. 37 p. 187.

Komarek, J. et al; Ringworm of cattle —results of vaccination; Veterinarniho Ustavu (1982) No. 12 pp. 69–74.

J.M.B. Smith et al; Strategies for the development of a vaccine against ringworm; Journal of Medical and Veterinary Mycology (1995) vol. 33 pp. 87–91.

A. Rybnikar et al; Vaccination of Horses Against Trichophytosis; ACTA Vet Brno (1991) vol. 60 pp. 165–169.

A. Rybnikar et al; Immunity in cattle vaccinated against ringworm; Mycoses (1991) vol. 34 pp. 433–436.

J.M. McGregor et al; Possible mechanisms of immune modulation in chronic dermatophytoses: an in votro study; British Journal of Dermatology (1992) vol. 127 pp. 233–238.

P.J. Gordon et al; Efficacy of a live attenuated Trichophyton verrucosum vaccine for control of bovine dermatophytosis; Veterinary Record (1996) vol. 139 pp. 395–396.

A. KH. Sarkisov et al; Modern Methods for Control of Animal Dermatomycosis; Advance in Agriultural Science (1987) pp. 181–197.

A. Tager et al; Immunotherapy of Superficial Dermatomycoses; Dermatologica (1973) vol. 147 pp. 123–129.

P. Kielstein; Sustematic control of dermatophytosis profunda of cattle in the former GDR; Mycoses (1990) vol. 33 pp. 575–579.

D.J. Deboer et al; In vestigations of a killed dermatophyte cell–wall vaccine against infection with Microsporum canis in cats; Research in Vet Sci. (1995) vol. 59 No. 2 pp. 110–113.

Karen A. Moriello et al; Feline Dermatophytosis; Feline Dermatology (1995) vol. 25 No. 4 pp. 901–921.

Perspectives on Cats; When the Fungus (Ringworm) Is Among Us; The Cornell Feline Health Center (1994) pp. 1–3 and 8.

Stanislaw; Med. Weterynaryjna (1987) vol. 43 pp. 259–264.

* cited by examiner

DERMATOMYCOSIS VACCINE

RELATED APPLICATIONS

The present application is a configuration of U.S. application Ser. No. 09/1256.915, filed Feb. 24, 1999, which is a continuation of U.S. application Ser. No. 08/1568,063, filed Dec. 6, 1995, now abandoned, which is a continuation of U.S. application Ser. No. 08/281,380, filed July 26, 1994, now abandoned, which is a continuation of U.S. application Ser. No. 08/1081,299 filed Aug. 11, 1993, now abandoned which is the National Stage of PCT/EP92/02391, filed Oct. 17, 1992, which claims priority under 35 USC § 119 to Russian Federation application Serial No. 50069611307308, filed Oct. 21, 1991; and claims priority benefit of all the above-listed applications.

BACKGROUND

This invention relates to the preperation of vaccines and their use in preparing compositions for specifically preventing and treating dermatomycosis.

Dermatomycoses in animals are anhropozoonotic diseases of the skin and related tissue. Clinical symptoms are characterized by loss of hair in the affected area, hyperemia, scaling and asbestos-like scabs. Inflammation is often accompanied by suppuration. Dermatomycoses are often also characterized by localized infection of the skin.

Dermatomycoses in animals carry a substantial socioeconomic impact. Diseased animals required prolonged treatment and can spread infection to both animals and humans.

Up till now, dermatomycoses have been treated using various types of medication applied locally to affected areas of the skin. These included the ointments YaM, Yuglon (I) and a number of other ointments, liniments, solutions and other substances containing fungicides and fungistatic agents.

The disadvantages of such treatments were:

they were not very effective;

they required the adoption of quarantine measures and disinfection of areas where animals were kept (rearing pens, vivaria, farms, zoos, circuses, etc);

they required substantial funds to be spent on drug preparations and veterinary treatment;

they posed difficulties in immobilizing the animals (for wild animals held in captivity).

Later vaccines were developed to treat trichophytosis in cattle (see USSR Patent No. 268593, 1970), fur-bearing animals and rabbits (see USSR Patent No. 835446, 1980), camels (see USSR Patent No. 1190574, 1985) and others.

A vaccine had also been developed earlier for the prevention and treatment of trichophytosis in horses: S-P-I (see USSR Patent No. 548947, 1976).

The S-P-I vaccine contains the vaccinal strain *Trichophyton equinum* No. 2251/71, deposited with the USSR All-Union State Scientific Control Institute of Veterinary Preparations, which is cultivated in agar/wort for 20–25 days at a temperature of 26–28° C. The fungal mass is then lifted from the surface of the nutrient medium, mixed with sterile distilled water and homogenized, and the concentration of cells is brought to 600–900 million per ml. The homogenate is transferred to a separate flask and stabilized with a mixture containing 2–8% gelatine (gelatose) and 10–40% sucrose in the ratio 1:1 (±25%), then lyophilized.

For prophylactic and treatment purposes the vaccine is injected into the muscle tissue of the neck area of juvenile and mature horses in two doses of 1–2 cc, depending on the age of the horse, with an interval of 10–14 days. For therapeutic use the dosages were doubled.

Vaccines obtained using this method have the disadvantage that they do not provide immunity against microsporiae and trichophytiae caused by other agents. It has also been noted that the areas where a live vaccine is injected may become a specific focus in which cultures of vaccinal strains may at certain times be produced. Given that some species of domestic animals come into frequent contact with humans, the occurrence of such specific foci in these animals is unacceptable.

DESCRIPTION

This invention now provides universal inactivated vaccines for the specific treatment and prevention of dermatomnycosis in animals and corresponding immunogenic fungal strains.

This aim has been achieved by using the following fungal strains as vaccial strains: *Trichophyton verrucosum* (especially No. VKPGF-931/410), *Trichophyton mentagrophytes* (especially No. VKPGF-930/1032), *Trichophyton equinum* (especially No. VKPGF-929/381), *Trichophyton sarkisovii* (especially No. VKPGF-551/68), *Microsporum canis* (especially No. VKPGF-928/1393), *Microsporum canis* var. *obesum* (especially No. VKPGF-727/1311), *Microsporum canis* var. *distortum* (especially No. VKPGF-728/120), *Microsporum gypseum* (especially No. VKPGF-729/59). Vaccines can be produced by using various combinations of antigenic material from the above strains together with a suitable carrier.

A preferred combination consists of *Trichophyton verrucosum* No. VKPGF-931/410, *Trichophyton mentagrophytes* No. VKPGF-930/1032, *Trichophyton equinum* No. VKPGF-929/381, *Microsporum canis* No. VKPGF-928/1393, *Microsporum canis* var. *obesum* No. VKPGF-727/1311, *Microsporum canis* var. *distortum* No. VKPGF-728/120, *Microsporum gypseum* No. VKPGF-729/59, particularly for use in dogs, cats and horses.

Another preferred combination of vaccine strains consists of *Trichophyton verrucosum* No. VKPGF-931/410, *Trichophyton mentagrophytes* No. VKPGF-930/1032, *Trichophyton sarkisovii* No. VKPGF-551/68, particularly for use in cattle.

The antigenic material may comprise a single antigen of at least one, and more particularly of all of the above-mentioned dermatophytes or from a pluaity of antigens, provided that a sufficient immune response is stimulated to give resistance to a dermnatophyte infection. Antigenic material for such a purpose can be prepared using methods known from the prior art, e.g., homogenizing the above-mentioned dermnatophytes or parts thereof, fractionation of dermatophyte preparations, production of antigenic dermatophyte material by recombinant DNA technology, etc. It is preferable to use homogenized culture material having 40 to 12-million, preferably 90 million microconidia.

Suitable physiologically acceptable carriers for administering the vaccines are known from the prior art and may include buffers, gels, microparticles, implantable solids, solutions and other adjuvants.

To kill off the dermatophytes it is possible to use thiomersal ($C_9H_9O_2SNaHg$), formaldehyde or 2-propiolactone.

In order to prepare a vaccine the following procedure may be used, for example:

Cultures of the strains are homogenized in an aqueous solution containing 0.2 ti 2.0% fermented, hydrolyzed muscle protein (FGM-s), 5 to 12% glucose and 0.1 to 1.2% yeast ha extract The concentration of the microconidia is adjusted to 40 to 120 million per milliliter and after 1 to 2 days the mixture is inactivated, e.g., with thiomersal ($C_9H_9O_2SNaHg$) in the ration 1:10,000 to 1:25,000, or with another substance known from the prior art. The resulting suspension is packaged and is ready for use in animals.

The preparation of the vaccines, the dosage to be given and the method of administration for prevention and therapeutic treatment are explained in Examples 1 to 3.

The invention now makes it possible to prepare an inactivated vaccine that reduces the probability of reinfection and also implants a high degree of immunity. Unlike the known vaccines the vaccine according to the invention in practice gives immunity to all important causes of dernatomycosis in animals.

Briefly, the vaccine according to the invention offers the following advantages:

- in many species of disease-prone animals it establishes immunity after intramuscular injection,
- it grants immunity against almost all causes of dermatomycosis in animals,
- it has stable immunogenic properties,
- it is easy to prepare,
- it has a complete set of exo- and endo-antigens of dermatophyte cultures and shows no side reactions in animals.

The vaccine has been successfully tested on over 500 animals of different species, predominantly in affected regions.

The strains used to produce the vaccine have been deposited at the "All-Union Collection of Pathogenic Fungi within the USSR, Ministry of Health Centre for Deep Mycoses" in Leningrad and at the "DSM—Deutsche Sammlung von Mikroorganismen und Zellkulturen", Mascheroder Weg 1B, W-3300 Braunschweig, Germany.

The following microorganisms were deposited with the Deutsche Samnmlung von Mikroorganismen und Zellkulturen (DSM) on Oct. 1, 1992 and received the following accession numbers:

- *T. verrucosum* VKPGF-931/410 received accession No. DSM 7277
- *T. mentagrophytes* VKPGF-930/1032 received accession No. DSM 7279
- *T. equinum* VKPGF-929/381 received accession No. DSM 7276
- *T. sarkisovii* VKPGF-551/68 received accession No. DSM 7278
- *M. canis* VKPGF-928/1393 received accession No. DSM 7281
- *M. canis* var. *obesum* VKPGF-727/1311 received accession No. DSM 7280
- *M. canis* var. *distortum* VKPGF-728/120 received accession No. DSM 7275
- *M. gypseum* VKPGP-729/59 received accession No. DSM 7274.

DSM is located at Macheroder Weg 1B, W-3300 Braunschweig, Germany. "T" is an abbreviation for Trichophyton and "M" is an abbreviation for Microsporum.

Their characteristics are set out below:

*Trichophyton verrucosum*, No. VKPGF-931/410

The strain was deposited at the DSM—Deutschc Sammlung von Mikroorganismen und Zellkulturen", Mascheroder Weg 1B, W-3300 Braunschweig, Germany.

The strain was obtained by directed selection based on spore production and attenuation of the epizootic Strain No. 410, which was identified on a deer in 1978. The strain was identified using the Rebell-Taplin key (Rebell, G., Taplin, D.: Dermatophytes, their recognition and identification, 1978) and according to Kashkin, P. N. et al. (Opredelitel patogennykn, toksigenykh vrednykh dlya cheloveka gribov, 1979).

The biological properties of the strain are described in Table 1.

Strain No. VKPGF-931/410 differs from the epizootic strain in its faster growth in nutrient medium, the enormous production of microconidia, lower virulence and the absence of any reaction with its antigens.

*Trichophyton mentagrophytes* No. VKPGF-930/1032

The strain was deposited at the DSM—Deutsche Sammlung von Mikroorganismen und Zellkulturen", Mascheroder Weg 1B, W-3300 Braunschweig, Germany.

The strain was obtained by directed selection based on spore production and attenuation of the epizootic Strain No. 1032, which was found on a horse in 1985. The strain was identified as described above Rebel, Taplin, loc. cit. and Kashkin, loc. cit.). The biological properties are described in Table 2.

Strain No. VKPGF-930/1032 differs from the epizootic strain by its faster growth in nutrient medium, the enormous production of microconidia, its lower virulence and the absence of any reaction with its antigens.

*Trichopyton equinum* No.VKPGF-929/381

The strain was deposited at the DSM—Deutsche Sammlung von Mikroorganismen und Zellkulturen", Mascheroder Weg 1B, W-3300 Braunschweig, Germany.

The strain was obtained by directed selection based on spore production and attenuation of the epizootic Strain No. 381 which was found on a horse in 1986. The strain was identified as describe above Rebel, Taplin, loc. cit. and Kashkin, loc. cit.). The biological properties are described in Table 3.

Strain No. VKPGF-929/381 differs from the epizootic strain by its faster growth in nutrient medium, lower virulence and the absence of any reaction with its antigens.

*Microsporum canis* No. GF-928/1393

The strain was deposited at the DSM—Deutsche Sammlung von Mikroorganismen und Zellkulturen", Mascheroder Weg 1B, W-3300 Braunschweig, Germany.

The strain was obtained by directed selection based on spore production and attenuation of the epizootic Strain No. 1393 which was found on a cat in 1988. The strain was identified as describe above Rebel, Taplin, loc. cit. and Kashkin, loc. cit.). The biological properties are described in Table 4.

Strain No. VKPGF-928/1393 differs from the epizootic strain by its faster growth in nutrient medium, its enormous capacity to carry spores, lower virulence and the absence of any reaction with its antigens.

*Microsporum canis* var. *obesum* No. VKPGF-727/1311

The strain was deposited at the DSM—Deutsche Sammiung von Mikroorganismen und Zellkulturen", Mascheroder Weg 1B, W-3300 Braunschweig, Germany.

The strain was obtained by directed selection based on spore production and attenuation of the epizootic Strain No. 1311 which was found on a tiger in 1986. The strain was identified as describe above Rebel, Taplin, loc. cit. and Kashkin, loc. cit.). The biological properties are described in Table 5.

Strain No. VKPGF-727/1311 differs from the epizootic strain by its faster growth in nutrient medium, its enormous capacity to carry spores, lower virulence and the absence of any reaction with its antigens.

*Microsporum canis* var. *distortum* No. VKPGF-728/120

The strain was deposited at the DSM—Deutsche Sammlung von Mikroorganismen und Zellkulturen", Mascheroder Weg 1B, W-3300 Braunschweig, Germany.

The strain was obtained by directed selection based on spore production and attenuation of the epizootic Strain No. 120 which was found on a black panther in 1987. The strain was identified as describe above Rebel, Taplin, loc. cit. and Kashkin, loc. cit.). The biological properties are described in Table 6.

Strain No. VKPGF-728/120 differs from the epizootic strain by its faster growth in nutrient medium, its enormous production of microconidia, its lower virulence and the absence of any reaction with its antigens.

*Microsporum gypseum* No. VKPGF-729/59

The strain was deposited at the DSM—Deutsche Sammlung von Mikroorganismen und Zellkulturen", Mascheroder Weg 1B, W-3300 Braunschweig, Germany.

The strain was obtained by directed selection based on spore production and attenuation of the epizootic Strain No. 59 which was found on a horse in 1985. The strain was identified as describe above Rebel, Taplin, loc. cit. and Kashkin, loc. cit.). The biological properties are described in Table 7.

Strain No. VKPGF-729/59 differs from the epizootic strain by its faster growth in nutrient medium, the enormous production of microconidia, the lower virulence and the absence of any reaction with its antigens.

TABLE 1

| Properties and characteristics of strain | Strain No. VKPGF-931/410 | Epizootic Strain No. 410 |
|---|---|---|
| Description of culture | Mature 10–15 day single-spore colony in agar/wort; white, velvety, convex, narrow growing margin undersurface colorless, colony diameter 10–15 mm | Mature 25–30 day colony in agar/wort; cream, leathery/velvety, folded, undersurface colorless, colony diameter 9–13 mm |
| Morphological characteristics | Mature 10–15 day culture with septate branching hyphae 1–3 $\mu$m wide, numerous oval, pyriform microconidia measuring 1.5 to 3 × 3 to 5 $\mu$m, no macroconidia | Mature 25–30 day culture with septate branching mycelium 1–3 $\mu$m wide, few oval, pyriform, cylindrical microconidia measuring 1 to 3 × 3 to 7 $\mu$m, single elongate irregular shape macroconidia with 2–5 septates measuring 3 to 5 × 25 to 30 $\mu$m, numerous arthrospores in chains 6–8 $\mu$m diameter, chlamydospores 10–12 $\mu$m diameter |
| Pathogenic characteristics | | |
| 12 to 15 days after application of a dose of 500–600 thousand cells of fungal matter per cm$^2$ to the scarified skin of a rabbit | Thin necrotic scabs | Dense asbestos-like scabs, possible suppuration |
| Spontaneous recovery after | 19–20 days | 25–30 days |
| Reaction response | | |
| Results of subcutaneous and intramuscular injection of inactivated corpuscular antigens from cultures | No observed changes in clinical state | Inflammation at point of injection, edema |
| Antigen response | | |
| 20 to 25 days after injecting rabbits with corpuscular antigens, antibody titers observed in blood serum | | |
| By Passive Hemagglutination Reaction (PHR) | 1:320 to 1:640 | 1:320 to 1:640 |
| By Enzyme-linked Immunosorbent Assay (ELISA) | 1:400 to 1:1600 | 1:400 to 1:1600 |
| Immunogenic response | | |
| Immunization of a group of rabbits with inactivated antigens from cultures (repeated at least 5 times) | Establishes immunity | Establishes immunity |

TABLE 2

| Properties and characteristics of strain | Strain No. VKPGF-930/1032 | Epizootic Strain No. 1032 |
| --- | --- | --- |
| Description of culture | Mature 10–15 day colony in agar/wort; cream, velvety/powdered, flat with slight flat elevation in center, narrow growing margin, fringed, undersurface light brown, colony diameter 25–30 mm | Mature 25–30 day colony in agar/wort; white, flat, narrow growing margin, undersurface reddish-brown, colony diameter 15–20 mm |
| Morphological characteristics | Septate, branching hyphae 1–3 μm wide, numerous pyriform, oval microconidia measuring 1 to 3 × 2 to 6 μm, no macroconidia | Septate, branching straight and spiral hyphae 1–3 μm wide, round, flattened pyriform microconidia measuring 1 to 3 × 2 to 6 μm, few elongate-oval macroconidia with 2–5 septates, measuring 2 to 6 × 15 to 25 μm |
| Pathogenic characteristics | | |
| 9 to 10 days after application of a dose of 500–600 thousand cells of fungal matter per $cm^2$ to the scarified skin of a rabbit | Necrotic scabs | Dense, asbestos-like scabs |
| Spontaneous recovery after | 22–25 days | 30–35 days |
| Reaction response | | |
| Results of subcutaneous and intramuscular injection of inactivated corpuscular antigens from cultures | No observed changes in clinical state | Inflammation at point of injection, edema |
| Antigen response | | |
| 20 to 25 days after injecting rabbits with corpuscular antigens, antibody titers observed in blood serum | | |
| By PHR | 1:320 to 1:640 | 1:320 to 1:640 |
| By ELISA | 1:400 to 1:1600 | 1:400 to 1:1600 |
| Immunogenic response | | |
| Immunization of a group of rabbits with inactivated antigens from cultures (repeated at least 5 times) | Establishes immunity | Establishes immunity |

TABLE 3

| Properties and characteristics of strain | Strain No. VKPGF-929/381 | Epizootic Strain No. 381 |
| --- | --- | --- |
| Description of culture | Mature 10–15 day colony in agar/wort; white, velvety/powdery, flat with slight elevation in center, narrow growing margin, fringed, undersurface light brown, colony diameter 15–20 mm | Mature 15 day colony in agar/wort; white, velvety, slightly creased center, narrow growing margin, undersurface reddish-brown, colony diameter 13–15 mm |
| Morphological characteristics | Septate, branching hyphae 1–3 μm wide, numerous oval pyriform microconidia measuring 2 to 3 × 3 to 6 μm, no macroconidia | Septate, branching hyphae with coil end, 1–4 μm wide, few oval, pyriform microconidia measuring 2 to 3 × 3 to 7 μm, lobar macroconidia measuring 4 to 7 × 15 to 25 μm |
| Pathogenic characteristics | | |
| 10 to 12 days after application of a dose of 500–600 thousand cells of fungal matter per $cm^2$ to the scarified skin of a rabbit | Necrotic scabs | Asbestos-like scabs |
| Spontaneous recovery after | 20–22 days | 25–30 days |
| Reaction response | | |
| Results of subcutaneous and intramuscular injection of inactivated corpuscular antigens from cultures | No observed changes in clinical state | Inflammation at point of injection, edema |
| Antigen response | | |
| 20 to 25 days after injecting rabbits with corpuscular antigens, antibody titers observed in blood serum | | |
| By PHR | 1:320 to 1:640 | 1:320 to 1:640 |
| By ELISA | 1:800 to 1:1600 | 1:800 to 1:1600 |
| Immunogenic response | | |
| Immunization of a group of rabbits with inactivated antigens from cultures (repeated at least 5 times) | Establishes immunity | Establishes immunity |

TABLE 4

| Proprieties and characteristics of strain | Strain No. VKPGP-928/1393 | Epizootic Strain No. 1393 |
| --- | --- | --- |
| Description of culture | Mature 10–15 day colony in agar/wort; white, fluffy, convex, narrow growing margin, arachnoid, undersurface brown, colony diameter 30–35 mm diameter 20–25 mm | Mature 15 day colony in agar/wort; greyish-beige, arachnoid, powdery in center, growing margin fringed, Undersurface yellowish, colony |
| Morphological characteristics | Septate, branching hyphae 1–4 μm wide, numerous pyriform, cylindrical microconidia, few fusiform macroconidia with 3–11 septates, measuring 10 to 20 × 40 to 75 μm 45 to 85 μm | Septate, branching hyphae 2 to 6 μm wide, few pyriform, cylindrical microconidia measuring 1 to 3 × 3 to 7 μm, numerous fusiform macroconidia with 3–11 septates, measuring 10 to 20 × |
| Pathogenic characteristics | | |
| 9 to 11 days after application of a dose of 500–600 thousand cells of fungal matter per $cm^2$ to the scarified skin of a rabbit | Necrotic scabs | Dense, asbestos-like scabs |
| Spontaneous recovery after | 20–24 days | 25–45 days |
| Reaction response | | |
| Results of subcutaneous and intramuscular injection of inactivated corpuscular antigens from cultures | No observed changes in clinical state | Edema and inflammation at point of injection |
| Antigen response | | |
| 20 to 25 days after injecting rabbits with corpuscular antigens, antibody titers observed in blood serum | | |
| By PHR | 1:320 to 1:640 | 1:320 to 1:640 |
| By ELISA | 1:400 to 1:1600 | 1:400 to 1:1600 |
| Immunogenic response | | |
| Immunization of a group of rabbits with inactivated antigens from cultures (repeated at least 5 times) | Establishes immunity | Establishes immunity |

TABLE 5

| Properties and characteristics of strain | Strain No. VKPGF-727/1311 | Epizootic Strain No. 1311 |
| --- | --- | --- |
| Description of culture | Mature 10–15 day colony in agar/wort; white, fluffy, flat with a denser central dome-like elevation, narrow growing margin, fringed, undersurface colorless with brown center, colony diameter 30–35 mm | Mature 15 day colony in agar/wort; greyish, fasciculate/arachnoid with pieces of cottony white mycelium, growing margin fringed, undersurface brownish, colony diameter 23–28 mm |
| Morphological characteristics | Septate, branching hyphae 1–3 μm wide, numerous pyriform, oval and cylindrical microconidia measuring 1 to 3 × 3 to 7 μm, few short, elliptical, fusiform, elongate-oval macroconidia, some irregular shapes, less frequently "beaked", with 2–5 septates, measuring 11 to 20 × 25 to 50 μm | Septate, branching hyphae 1–5 μm wide, few oval, cylindrical microconidia measuring 1 to 3 × 3 to 8 μm, numerous elliptical, fusiform, elongate-oval or irregularly-shaped macroconidia with 2–5 septates, measuring 11 to 20 × 25 to 55 mm |
| Pathogenic characteristics | | |
| 12 to 15 days after application of a dose of 500–600 thousand cells of fungal matter per $cm^2$ to the scarified skin of a rabbit | Thin necrotic scabs | Dense, asbestos-like scabs |
| Spontaneous recovery after | 10–25 days | 25–30 days |
| Reaction response | | |
| Results of subcutaneous and intramuscular injection of inactivated corpuscular antigens from cultures | No observed changes in clinical state | Inflammation and edema at point of injection |
| Antigen response | | |
| 20 to 25 days after injecting rabbits with corpuscular antigens, antibody titers observed in blood serum | | |
| By PHR | 1:320 to 1:640 | 1:320 to 1:640 |
| By ELISA | 1:800 to 1:1600 | 1:806 to 1:1600 |
| Immunogenic response | | |
| Immunization of a group of rabbits with inactivated antigens from cultures (repeated at least 5 times) | Establishes immunity | Establishes immunity |

TABLE 6

| Properties and characteristics of strain | Strain No. VKPGF-728/120 | Epizootic Strain No. 120 |
|---|---|---|
| Description of culture | Mature 10–15 day colony in agar/wort; cream, velvety/powdery, button-like elevation in center, narrow growing margin, finely-fringed, undersurface light-brown with dark-brown center, colony diameter 25–30 mm | Mature 15 day colony in agar/wort; light-beige, powdery, umbonate, narrow growing margin, undersurface brown, colony diameter 1 8–20 mm |
| Morphological characteristics | Septate, branching hyphae 1–3 $\mu$m wide, numerous pyriform, oval, cylindrical microconidia measuring 1 to 3 × 3 to 8 $\mu$m, few irregular deformed macroconidia, distorted or fusiform with 2–9 septates, measuring 8 to 20 × 25 to 70 $\mu$m | Septate, branching hyphae 1–3 $\mu$m wide, few pyriform, oval, cylindrical microconidia measuring 1 to 3 × 3 to 8 $\mu$m, numerous irregular deformed or fusiform macroconidia with 2–9 septates, measuring 8 to 20 × 25 to 80 $\mu$m |
| Pathogenic characteristics | | |
| 12 to 15 days after application of a dose of 500–600 thousand cells of fungal matter per cm$^2$ to the scarified skin of a rabbit | Thin necrotic scabs | Asbestos-like scabs |
| Spontaneous recovery after | 20–25 days | 27–45 days |
| Reaction response | | |
| Results of subcutaneous and intramuscular injection of inactivated corpuscular antigens from cultures | No observed changes in clinical state | Inflammation and edema at point of injection |
| Antigen response | | |
| 20 to 25 days after injecting rabbits with corpuscular antigens, antibody tilers observed in blood serum | | |
| By PHR | 1:320 to 1:640 | 1:320 to 1:640 |
| By ELISA | 1:800 to 1:1600 | 1:500 to 1:1600 |
| Immunogenic response | | |
| Immunization of a group of rabbits with inactivated antigens from cultures (repeated at least 5 times) | Establishes immunity | Establishes immunity |

TABLE 7

| Properties and characteristics of strain | Strain No. VKPGF-729/59 | Epizootic Strain No. 59 |
|---|---|---|
| Description of culture | Mature 10–1 5 day colony in agar/wort; white, velvety/fluffy, flat with slight elevation in center of colony, flat growing margin, undersurface brownish, colony diameter 25–30 mm | Mature 15 day colony m agar/wort; cream, velvety/powdery, flat with fluffy white mycelium in center, thin growing margin, undersurface brownish, colony diameter 20–22 mm |
| Morphological characteristics | Septate, branching hyphae 2–3 $\mu$m wide, numerous oval, pyriform, cylindrical microconidia measuring 2 to 4 × 3 to 6 $\mu$m, no or few macroconidia, elliptical, elongate-oval shape with 2–5 septates, measuring 7 to 15 × 25 to 40 $\mu$m | Septate, branching hyphae 2–5 $\mu$m wide, few oval, pyriform, cylindrical microconidia measuring 2 to 4 × 3 to 7 $\mu$m, numerous elliptical, stretched-oval macroconidia with 2–5 septates, measuring 7 to 15 × 25 to 50 $\mu$m |
| Pathogenic characteristics | | |
| 12 to 15 days after application of a dose of 500–600 thousand cells of fungal matter per cm$^2$ to the scarified skin of a rabbit | Thin necrotic scabs | Dense, asbestos-like scabs |
| Spontaneous recovery after | 20–22 days | 25–28 days |
| Reaction response | | |
| Results of subcutaneous and intramuscular injection of inactivated corpuscular antigens from cultures | No observed changes in clinical state | Inflammation at point of injection |
| Antigen response | | |
| 20 to 25 days after injecting rabbits with corpuscular antigens, antibody titers observed in blood serum | | |
| By PHR | 1:320 to 1:640 | 1:320 to 1:640 |
| By ELISA | 1:400 to 1:1600 | 1:400 to 1:1600 |
| Immunogenic response | | |
| Immunization of a group of rabbits with inactivated antigens from cultures (repeated at least 5 times) | Establishes immunity | Establishes immunity |

The vaccine may be prepared using the strain *Trichophyton sarkovii*, No. 551/68. It is described for example in USSR Patent No. 1177972 dated Aug. 8, 1985, to which reference is made in its entirety.

This strain was also deposited at the DSM—Deutsche Sammlung von Mikroorganismen und Zellkulturen, Mascheroder Weg 1B, W-3300 Braunschweig, Germany.

In particular, the invention relates to the following:

a dermatomycosis vaccine, characterized in that it contains antigenic material from at least one of the following dematophytes:

*Trichophyton verrucosum*, particularly *Trichophyton verrucosum* Strain No. VKPGF-931/410 and/or

*Trichophyton mentagrophytes*, particularly *Trichophyton mentagrophytes* Strain No. VKPGF-930/1032 and/or

*Trichophyton sarkisovii*, particularly *Trichophyton sarkisovii* Strain No. VKPGF-551/68 and/or

*Microsporum canis*, particularly *Microsporum canis* Strain No. VKPGF-928/1393 and/or

*Microsporum canis* var. *obesum*, particularly *Microsporum canis* var. *obesum* Strain No. VKPGF-727/131 and/or

*Microsporwn canis* var. *distortum*, particularly *Microsporum canis* var. *distortum* Strain No. VKPGF-728/120 and/or

*Microsporum gypseum*, particularly *Microsporum gypseum* Strain No. VKPGF-729/59, and a physiologically acceptable carrier.

a dermatomycosis vaccine, particularly as an agent for treating dogs, cats and horses, characterized in that it contains antigenic material from the dermatophyte strains *Trichophyton verrucosum* No. VKPGF-931/410, *Trichophyton mentagrophytes* No. VKPGF-930/1032, *Trichophyton equinum* No. VKPGF-929/381, *Trichophyton sarkisovii* Strain No. VKPGF-551/68, *Microsporum canis* No. VKPGF-928/1393, *Microsporum canis* var. *obesum* No. VKPGF-727/311, *Microsporum canis* var. *distortum* No. VKPGF-728/120, *Microsporum gypseum* No. VKPGF-729/59, together with a physiologically acceptable carrier.

a dermatomycosis vaccine, more particularly as an agent for treating cattle, characterized in that it contains antigenic material from the dermatophyte strains *Trichophyton verrucosum* No. VKPGF-931/410, *Trichophyton mentagrophytes* No. VKPGF-930/1032, *Trichophylon equinum* No. VKPGF-929/381, *Trichophyton sarkisovii* Strain No. VKPGF-551/68, together with a physiologically acceptable carrier.

a dermatomycosis vaccine as described above, characterized in that it contains 40 to 120 million, preferably 90 million microconidia, a dermatomycosis vaccine as described above, characterized in that it contains thiomersal or formaldehyde or 2-propiolactone as inactivator, a dermatomycosis vaccine as described above, characterized in that the physiologically acceptable carrier used is an aqueous solution containing 0.2 to 2.0 percent weight of fermented, hydrolyzed muscle protein, 5 to 12 percent weight glucose and 0.1 to 1.2 percent weight yeast extract, the dermatophyte strains:

*Trichophyton verrucosum* Strain No. VKPGF-931/410,

*Trichophyton mentagrophytes* Strain No. VKPGF-930/1032,

*Trichophyton equinum* Strain No. VKPGF-929/381,

*Microsporum canis* Strain No. VKPGF-928/1393,

*Microsporum canis* var. *obesum* Strain No. VKPGF-727/1311,

*Microsporum canis* var. *distortum* Strain No. VKPGF-728/120, and

*Microsporum gypseum* Strain No. VKPGF-729/59.

a process for preparing a vaccine, characterized in that:

a. antigenic material is prepared from at least one of the following strains:

*Trichophyton verrucosum* Strain No. VKPGF-931/410,

*Trichophyton mentagrophytes* Strain No. VKPGF-930/1032,

*Trichophyton sarkovii* Strain No. VKPGF-551/68,

*Microsporum canis* Strain No. VKPGF-928/1393,

*Microsporum canis* var. *obesum* Strain No. VKPGF-727/1311,

*Microsporum canis* var. *distortum* Strain No. VKPGF-728/120,

*Microsporum gypseum* Strain No. VKPGF-729/59, and b. the antigenic material is mixed with a physiologically acceptable carrier.

a process as described above, characterized in that an agent, particularly thiomersal, formaldehyde or 2-propiolactone is added to inactivate the dermatophytes.

The invention is illustrated by means of the Examples that follow.

EXAMPLES

Example 1

To produce 1 liter of vaccine, cultures are taken of the strains VKPGF-931/410, 930/1032, 929/381, 551/68, 928/1393, 727/1311, 728/120, and 729/59 and grown in agar/wort at 26° C. for 15 days. Each culture is grown in 8 mattress flasks. The fungal mass is then lifted off, homogenized, placed in 200 ml of solution and added to each mixer. The solution used is an aqueous solution containing 1% fermented hydrolyzed muscle protein, 10% glucose and 1% yeast extract The concentration of microconidia is brought to 90 million per ml of homogenate. After 2 days, 125 ml of each culture in suspension is taken and mixed in a single container. The vaccine may be prepared by mixing together various combinations of the given strains.

To inactivate the homogenate mixture, thiomersal is added directly to the cell suspension in the ration 1:20,000. 50 mg of thiomersal is added for every liter of homogenate. The cell mixture is allowed to stand at room temperature for 2 days.

The resulting vaccine is bottled, checked for sterility, safety and immunogenic properties in accordance with accepted methods, and kept refrigerated at 4° C.

Vaccine produced in this manner was used to immunize animals.

For prophylactic and treatment purposes the vaccine was used in the following doses (see Table 8):

TABLE 8

| Animal family | Age | Site of injection | Dosage (ml) Prophylactic | Dosage (ml) Treatment |
|---|---|---|---|---|
| Felidae medium/ large cats | 1–6 months | Gluteal muscles | 2–5 | 3–6 |
| | 6 months + | Gluteal muscles | 3–7 | 4–10 |
| Small cats | 1–5 months | Gluteal muscles | 1–1.5 | 1–1.5 |
| | 5 months + | Gluteal muscles | 1–2 | 1–2 |

TABLE 8-continued

| Animal family | Age | Site of injection | Dosage (ml) Prophylactic | Dosage (ml) Treatment |
|---|---|---|---|---|
| Ursidae | 1–12 months | Gluteal muscles | 1–3 | 3–5 |
|  | 12 months + | Guinea muscles | 3–5 | 5–6 |
| Procyonidae | 1–10 months | Gluteal muscles | 0.3–0.5 | 0.5 |
|  | 10 months + | Gluteal muscles | 0.3–0.5 | 0.5–1.0 |
| Viverridae | 1–12 months | Gluteal muscles | 0.3–0.5 | 0.5 |
|  | 12 months + | Gluteal muscles | 0.5–1.0 | 0.5–1.0 |
| Hyaenidae | 1–12 months | Gluteal muscles | 1–3 | 1–3 |
|  | 12 months | Gluteal muscles | 3–5 | 5–6 |
| Canidae | 1–10 months | Gluteal and | 0.3–0.5 | 0.5–1.0 |
|  | 10 months + | shoulder muscles | 0.3–1.0 | 0.5–1.0 |
| Equidae | 3–12 months | Neck area | 0.3–0.5 | 0.5–1.0 |
|  | 12 months + | Neck area | 0.5 | 0.5–1.0 |
| Tyropodae | 1–6 months | Shoulder and | 3–5 | 5–10 |
|  | 6 months + | neck area | 5–8 | 7–10 |
| Bovidae | 1–12 months | Neck area | 3–5 | 5–10 |
|  | 12 months | Neck area | 5–8 | 7–10 |

Example 2

The vaccine produced by the method described in Example 1 was tested on laboratory animals and various other animals for effectiveness in the prevention and treatment of disease. The results are given in Table 9.

Example 3

The vaccine produced by the method described in Example 1 was also used to treat animals suffering from dermatophytiae. The results are given in Table 10.

TABLE 9

| Type of animals | Number | Dosage (cm$^3$) | Effectiveness |
|---|---|---|---|
| Rabbits | 10 | 1.0 | No symptoms of disease after infection with virulent cultures of the fungi T. mentagrophytes, T. verrucosum, T. equinum, M. canis, M. gypseum. |
| Dogs | 5 | 0.3 | |
| Domestic cats | 3 | 1.0 | |
| Horses | 5 | 0.5 | No dermatophytiae linked to the fungi M. canis and T. mentagrophytes after being in direct contact with diseased animals. |
| Ponies | 3 | 0.3 | |
| Camels | 2 | 5.0 | |
| Bears | 2 | 3.0 | |
| Leopards | 2 | 4.0 | |
| Hyenas | 2 | 2.0 | No dermatophytiae linked to the fungi M. canis and T. mentagrophytes after being in direct contact with sources of infection. |
| Servals | 2 | 3.0 | |
| Ocelots | 2 | 2.0 | |
| Lions | 2 | 3.0 | |
| Tigers | 3 | 7.0 | |
| Nasuas | 3 | 0.5 | |
| Civets | 2 | 1.0 | |
| Rabbits | 7 | 1.5 | No symptoms of disease after infection with virulent cultures of the fungi T. sarkisovii and M. gypseum. |
| Dogs | 3 | 0.5 | |
| Domestic cats | 3 | 1.5 | |
| Black panthers | 2 | 5.0 | No dermatophytiae linked to the fungi M. canis, T. mentagrophytes and T. verrucosum after being in direct contact with sources of infection. |
| Tigers | 5 | 7.0 | |
| Geese | 6 | 3.0 | |
| Bears | 3 | 1.0 | |
| Dogs | 8 | 0.5 | |
| Llamas | 2 | 3.0 | |

TABLE 10

| Type of animals | Number | Dosage (cm$^3$) | Effectiveness |
|---|---|---|---|
| Black panthers | 5 | 7.0 | Affected by microsporosis linked to the fungi M. canis. Recovery took place 12–25 days after immunization. |
| Black panthers | 3 | 4.0 | |
| Horses | 3 | 1.0 | |
| Ponies | 2 | 0.5 | |
| Lions | 3 | 10 | |
| Tigers | 3 | 10 | |
| Dogs | 4 | 0.5 | |
| Bear | 1 | 5.0 | |
| Hyena | 1 | 5.0 | |
| Domestic cats | 15 | 1.5 | Affected by microsporosis linked to the fungi M canis. Recovery took place 10–20 days after immunization. |
| Dogs | 5 | 0.5 | |
| Horses | 5 | 0.7 | |
| Black panther | 1 | 6.0 | Affected by trichophytosis linked to the fungi T. mentagrophytes. Recovery took place 12–15 days after immunization. |
| Red foxes | 4 | 1.0 | |
| Bears | 2 | 5.0 | |
| Mountain sheep | 1 | 7.0 | |
| Horses | 15 | 1.0 | Affected by microsporosis linked to the fungi M. equinum. Recovery took place 12–20 days after immunization. |

Bibliograhy (1) Aisenberg, A. A., Noskow, A. I., Kolovatsky, P. P. "Primenenie Yuglona v Veterinarii" in Scientific and Technical Information Bulletin of the State and Scientific Control Committee under the Moldavian Council of Ministers (1958), p. 88.

(2) USSR Patent No. 548947 (1976).

What is claimed is:

1. A dermatomycosis vaccine comprising inactivated dermatophytes, wherein the inactivated dermatophytes consist of: Trichophyton verrucosiun Strain No. VKPGF-931/410 (accession No. DSM 7277), Trichophyton mentagrophytes Strain No. VKPGF-930/1032 (accession No. DSM 7279), Trichophyton sarkisovii Strain No. VKPGF-551/68 (accession No. DSM 7278), Trichophyton equinum Strain No. VKPGF-929/381 (accession No. DSM 7276), Microsporum canis Strain No. VKPGF-928/1393 (accession No. DSM 7281), Microsporum canis var. obesum Strain No. VKPGF-727/1311 (accession No. DSM 7280), Microsporm canis var. distortum Strain No. VKPGF-728/120 (accession No. DSM 7275), and Microsporum gypseum Strain No. VKPGF-729/59 (accession No. DSM 7274).

2. A dermatomycosis vaccine comprising inactivated dermatophytes, wherein the inactivated dermatophytes consist of: Trichophyton verrucosum Strain No. VKPGF-931/410 (accession No. DSM 7277), Trichophyton mentagrophytes Strain No. VKPGF-930/1032 (accession No. DSM 7279), and Trichophyton sarkisovii Strain No. VKPGF-551/68 (accession No. DSM 7278).

* * * * *